(12) United States Patent
Abraham et al.

(10) Patent No.: US 8,919,368 B2
(45) Date of Patent: Dec. 30, 2014

(54) SELF-LOCKING T-PIECE

(71) Applicant: Dräger Medical GmbH, Lübeck (DE)

(72) Inventors: Klaus Abraham, Lübeck (DE); Gerd Wotha, Warnsdorf (DE); David Michael Samways, Malente-Krummsee (DE)

(73) Assignee: Dräger Medical GmbH, Lübeck (DE)

( * ) Notice: Subject to any disclaimer, the term of this patent is extended or adjusted under 35 U.S.C. 154(b) by 120 days.

(21) Appl. No.: 13/682,082

(22) Filed: Nov. 20, 2012

(65) Prior Publication Data

US 2013/0126011 A1    May 23, 2013

(30) Foreign Application Priority Data

Nov. 21, 2011  (DE) .......................... 10 2011 119 075

(51) Int. Cl.
| | |
|---|---|
| *F16K 13/00* | (2006.01) |
| *A61M 16/08* | (2006.01) |
| *A61M 16/20* | (2006.01) |
| *F16K 1/48* | (2006.01) |

(52) U.S. Cl.
CPC ................ *F16K 13/00* (2013.01); *A61M 16/08* (2013.01); *A61M 16/0816* (2013.01); *A61M 16/208* (2013.01); *F16K 1/48* (2013.01); *A61M 16/0833* (2013.01)

USPC ................ 137/15.18; 137/315.27; 251/149.1

(58) Field of Classification Search
USPC .......... 137/15.18, 315.01, 315.27; 251/149.1; 128/202.27, 202.24, 912
See application file for complete search history.

(56) References Cited

U.S. PATENT DOCUMENTS

| | | | |
|---|---|---|---|
| 4,951,661 A | 8/1990 | Sladek | |
| 6,725,858 B2 * | 4/2004 | Loescher | ................. 128/200.14 |
| 2002/0162554 A1 | 11/2002 | Loescher | |

\* cited by examiner

*Primary Examiner* — Kevin Lee
(74) *Attorney, Agent, or Firm* — McGlew and Tuttle, P.C.

(57) ABSTRACT

A self-locking T-piece connects an attachment to a breathing gas line. The self-locking T-piece has a line section (2), a connection line (4) branching off therefrom, a movable valve body (10) with a valve disk (12), and a valve seat (14). The valve body (10) is prestressed by a spring (16) into a position to seal the connection line (4) against the line section (2), with the valve disk in the valve seat, and moves out of the sealing position when connecting the attachment to the connection line. The valve body (10) is elastically deformable such that it can be advanced through the connection line (4) and the valve seat (14), while undergoing elastic deformation, and returns to its original shape during the entry of valve disk (12) into the line section, in which it has a sufficient extension to be able to cover the valve seat for sealing.

18 Claims, 4 Drawing Sheets

SELF-LOCKING T-PIECE

CROSS REFERENCE TO RELATED APPLICATIONS

This application claims the benefit of priority under 35 U.S.C. §119 of German Patent Application DE 10 2011 119 075.2 filed Nov. 21, 2011, the entire contents of which are incorporated herein by reference.

FIELD OF THE INVENTION

The present invention pertains to a self-locking T-piece for connecting an attachment to a breathing gas line, wherein the self-locking T-piece has a line section, a connection line branching off therefrom and a movable valve body with valve disk, which is prestressed by a spring into a position sealing the connection line against the line section and which is designed to be moved out of the sealing position when connecting the attachment to the connection line.

BACKGROUND OF THE INVENTION

Such a self-locking T-piece is known, for example, from US 2002/0162554 A1. The prior-art self-locking T-piece has a line section, at both ends of which flexible tubes of the breathing gas line can be connected. The connection line, which opens into the line section, is approximately at right angles to the line section. A valve body has a valve disk with an external diameter that is larger than the diameter of a valve seat at the end of the connection line. The valve seat may be formed by a continuation of the connection line into the interior of the line section; the valve disk has a larger external diameter in this case than the internal diameter of the connection line, so that it can cover the opening of the continuation of the connection line, which opening opens into the line section, in order to thus block the connection line. The valve body has, furthermore, a shaft, which carries the valve disk. A spring, which applies a force directed towards the connection line to the valve body, acts on the valve body, so that the valve disk is pulled onto the mouth opening of the connection line for sealing. The shaft of the valve body is connected to an end piece, which can slide in the connection line. This end piece forms an abutment for the spring and has the further task of lifting the valve body out of the sealing position thereof when an attachment is attached to the connection line, where said attachment has a line, which is inserted into the outer end of the connection line. When the line of the attachment is being pushed into the connection line, the attachment comes into contact with the end piece of the valve body and thus lifts the valve body out of the sealing position thereof at the mouth of the connection line. Conversely, the valve closes again when the attachment is again removed from the connection line by being pulled off.

Such self-locking T-pieces are used in mechanical respiration. Typical attachments, which are connected to a breathing gas line, are, for example, water traps, nebulizers and sensors. The valve is automatically opened during the mounting of the attachment and it closes again during the removal of the attachment. Such T-pieces are increasingly frequently used only for single-time use and are used at only one patient for the short-term use and are then disposed of. It is especially important in the case of such T-pieces for single-time use to build them with the smallest number of parts possible and to make the mounting operations during the assembly of the self-locking T-piece as simple as possible.

Another self-locking T-piece is known from U.S. Pat. No. 4,951,661 A. The self-locking T-piece has a valve body with U-shaped cross section, which carries a flexible valve membrane on its top side. A spring element presses the membrane and thus the U-shaped valve body from the tip, so that the valve membrane closes the opening of the connection line. When a device to be connected is inserted into the connection line, the U-shaped valve body is lifted thereby, as a result of which the valve membrane is likewise lifted out of the valve seat.

SUMMARY OF THE INVENTION

An object of the present invention is therefore to design a self-locking T-piece such that it has a small number of components and can be assembled in a simple manner, and to propose a manufacturing process therefor.

According to the present invention, a self-locking T-piece is provided comprising a line section, a connection line branching off from the line section, a spring, a movable valve body with a valve disk body and a valve seat. The valve body is prestressed by the spring into a sealing position with the valve disk in the valve seat, in which the valve disk seals the connection line relative to the line section, and is moved out of the sealing position when connecting the attachment to the connection line. The valve body is elastically deformable, such that the valve body can be advanced in the connection line and through the valve seat during elastic deformation. The valve body is elastically deformable, such that when the valve disk enters the line section, it returns beyond the valve seat to its original shape, in which it has a sufficient extension to be able to cover the valve seat for sealing at the end of the connection line.

The self-locking T-piece is characterized in that markedly fewer components and joining operations are needed to build up the valve in the T-piece. Namely, conventional T-pieces have the problem of bringing the valve disk having an extension greater than the internal diameter of the valve seat into position in the interior of the line section. It was, for example, common practice for this to provide a connecting branch continuing the connection line at the line section opposite the connection line, through which connecting branch the valve body with the valve disk thereof can be inserted and which the spring can likewise be inserted to generate the prestress (pretension) acting on the valve body. After inserting the valve components, the connecting branch can then be closed by a cover to be attached to the outer end thereof. However, this entails, on the whole, some effort during manufacture.

In case of the shape according to the present invention, the T-piece may be formed simply from a line section with a connection line branching off therefrom; consequently, no connecting branch is needed for mounting the valve body and spring. The valve body is, instead, designed as an elastically deformable valve body such that it can be pushed through the connection line and the valve seat from the outside to the inside, and the valve body will then return to its original shape beyond the valve seat when the valve disk enters the interior of the line section and the deforming force due to the connection line and the valve seat is eliminated as a result.

In a preferred embodiment, the valve body has a shaft and a disk body made of relatively hard plastic material, which said disk body is carried by said shaft, wherein the external diameter of the plastic disk is smaller than the internal diameter of the valve seat. The disk body carries, in turn, a collar made of a plastic material that is softer than that of the valve body, and said collar projects outwardly over the edge of the valve disk body. This projecting collar made of a softer plastic material is bent back rearwardly when the valve disk is pushed forward through the connection line and the valve seat. After exiting the connection line and entering the interior of the line section, the collar bent back rearwardly returns again into its original position essentially in parallel to the plane of the valve disk. As a result, the valve disk with the collar being carried thereby can cover the inlet mouth of the connection line in the line section, which said mouth forms the valve seat, and seal same as a result.

The projecting collar made of softer plastic material in one piece with the rest of the valve disk may be manufactured in a two-component injection molding process. As an alternative, the collar projecting over the valve body may also be manufactured as a separate part and connected to the disk body.

In another preferred embodiment, the valve body has a shaft, which is eccentrically connected to the disk body. By bending the shaft, the valve disk can be swung out rearwardly when pushing forward through the connection line and the valve seat and thus advanced up into the interior of the line section, after which the elastic bending of the shaft is elastically restored and the valve disk is brought into a position in which it covers the valve seat at the mouth of the connection line. The disk body itself can be elastically flexible in this embodiment to such an extent that it can be deformed while passing through the valve seat and can pass through same as a result. This would be the case, for example, with a round valve disk during passage through a valve seat with a smaller diameter. As an alternative, the valve disk could have a square shape. The square valve body could pass through a square valve seat with smaller dimensions (also referred to herein as dimension) in this case when the valve shaft is bent back, when the valve disk, aligned with a breadth extension, passes through the square valve seat in a diagonal of said square valve seat.

The present invention will be explained in more detail below on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
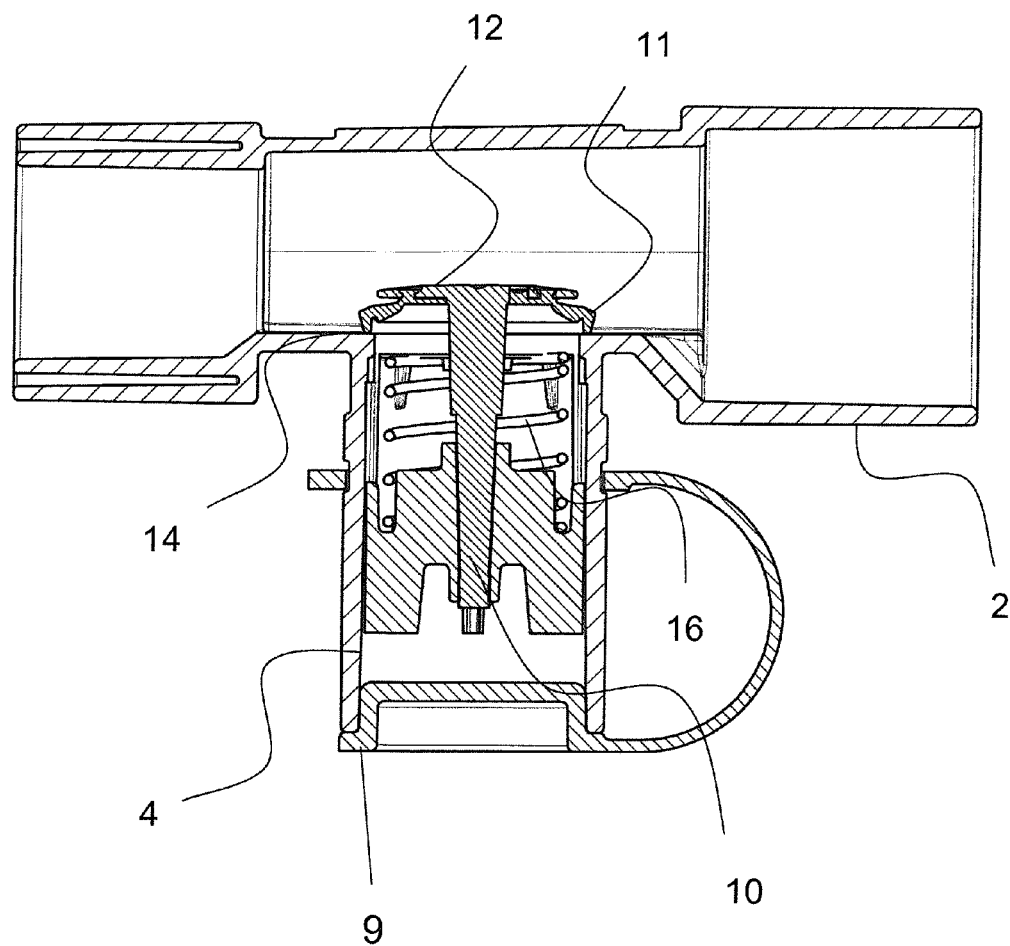
FIG. 1 is a cross-sectional view of a self-locking T-piece.

Referring to the drawings in particular, the T-piece shown in FIG. 1 has a line section 2, which can be inserted into a breathing gas line. A connection line 4, whose outer opening is closed by a removable cover 9, originates from line section 2 at right angles thereto. A movable valve body 10 has a valve disk 12, which is located in a valve seat 14 in the closed position. A spring 16 is supported at one end in the connection line 4 and rests with its other end at an end piece of valve body 10 located opposite the valve disk 12 and as a result pulls valve disk 12 into the closed position in the valve seat. When connecting an attachment, a connecting branch of the attachment is inserted after opening the cover 9 into connection line 4 and is advanced, so that it comes into contact with the end piece of valve body 10 and holds the valve open against the force of spring 16 when the attachment is mounted on connection line 4.

Figure 2:
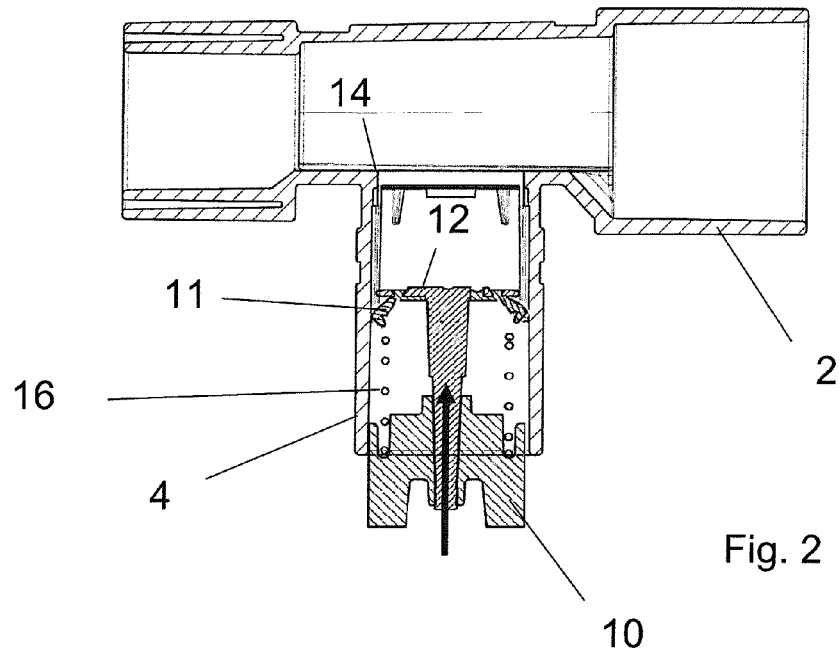
FIG. 2 is a cross-sectional view showing a first of consecutive stages during the mounting of the self-locking T-piece.
Figure 3:
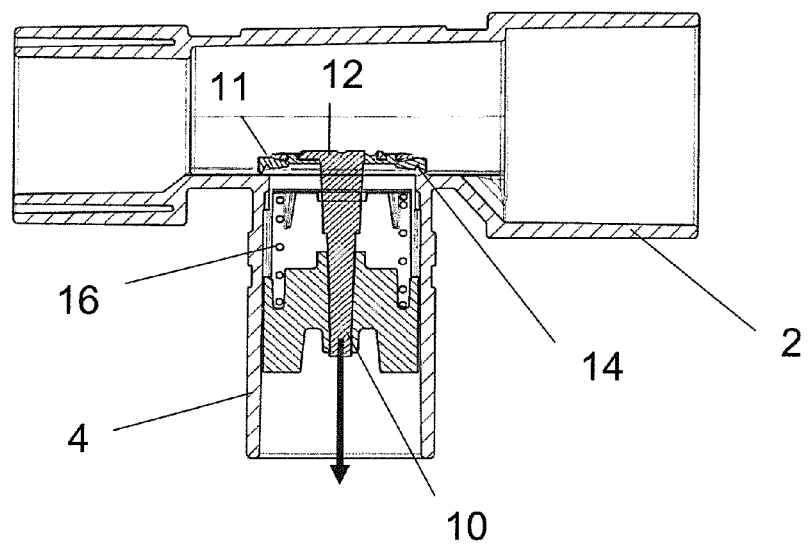
FIG. 3 is a cross-sectional view showing a second of consecutive stages during the mounting of the self-locking T-piece.

FIGS. 2 and 3 show lateral sectional views of a valve body 10 at different stages during mounting in a T-piece. In the view according to FIG. 2, valve body 10 is shown during mounting. Valve body 10 has a shaft and a valve disk 12. Valve disk body 12 is provided around the shaft with a projecting collar 11, which has a somewhat larger diameter (dimension) than valve disk body 12 and consists of a softer material than valve disk body 12. When installing the valve body 10, the latter is inserted with its valve disk 12 in the front into the outer end of connection line 4, where the valve disk body 12 has an external diameter (dimension) that is somewhat smaller than the internal diameter (dimension) of connection line 4, so that valve disk 12 can pass through the connection line. In the view in FIG. 2, valve body 10 is shown during insertion into connection line 4. Collar 11 of the valve disk is bent backward in this phase, because the external diameter (dimension) of collar 11 is larger than the internal diameter (dimension) of connection line 4. As soon as valve disk 12 with its collar 11 has reached the inner end of connection line 4, collar 11 widens again in the interior of line section 2 and thus it again attains a larger diameter (dimension) than the internal diameter (dimension) of connection line 4 and than valve seat 14, as is shown in FIG. 3. Valve seat 14 is formed in the embodiment shown by the mouth of connection line 4 in line section 2. Connection line 4 may also have a continuation extending into the interior of line section 2, and the upper edge of this connection line continuation now forms the valve seat. After insertion of the valve body, the outer opening of connection line 4 is closed by a cover 9 (FIG. 1). Spring 16 is in contact with its outer end with an end piece of valve body 10 and with its opposite end relative to the line section 2 in a supported manner, so that a force acting on valve body 10 in the direction indicated by the arrow in FIG. 3 acts on valve body 10 outwardly, as a result of which collar 11 of the valve disk body is pulled to come into contact with valve seat 14 and the valve is thus held in the closed position.

Figure 4:
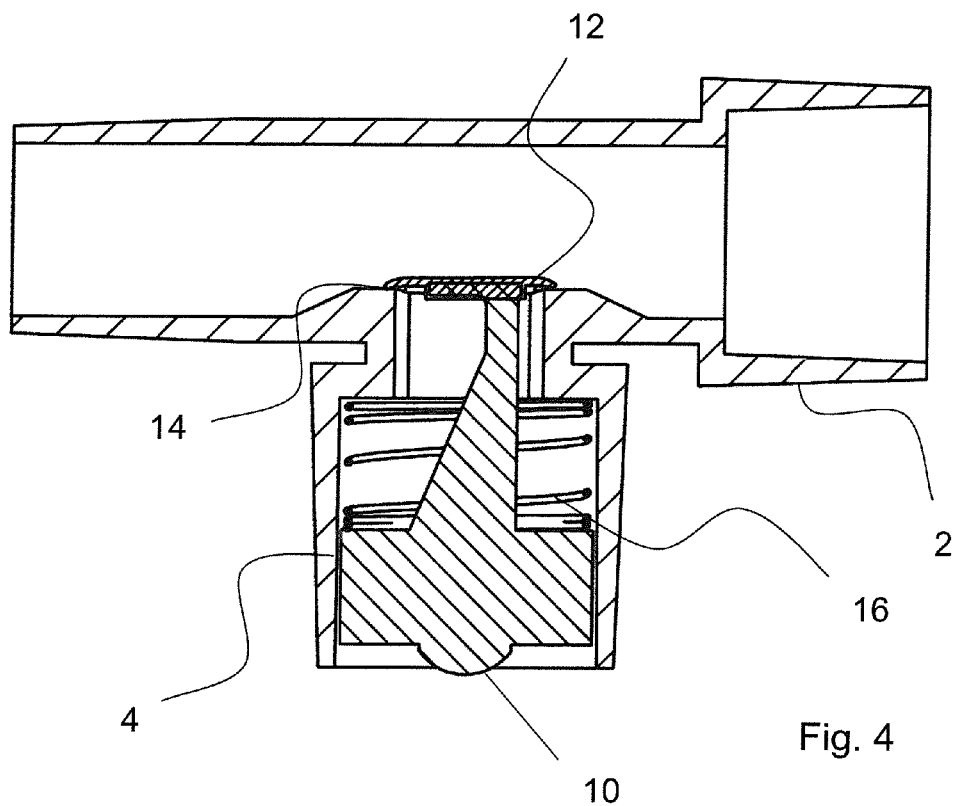
FIG. 4 is a cross-sectional view of an alternative embodiment of a self-locking T-piece.
Figure 5:
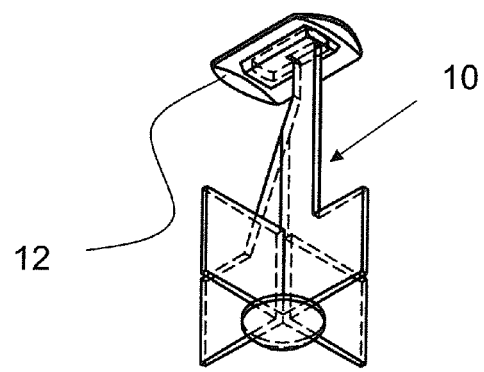
FIG. 5 is a perspective view of the valve body from the embodiment shown in FIG. 4.

FIGS. 4 and 5 show an alternative embodiment of the self-locking T-piece. The valve body has a shaft in this embodiment, which is located eccentrically in connection line 4, and its upper end is offset in the direction of one side. At this upper end the shaft carries an essentially rectangular valve disk 12. This rectangular valve disk 12 is bent, on the one hand, back while valve body 10 is being pushed into connection line 4 and is, in addition, bent in itself to the extent that it can pass through connection line 4 and valve seat 14. After entry into the interior of line section 2 beyond valve seat 14, the valve disk returns to its original shape at right angles to the shaft and thus covers the likewise rectangular valve seat 14, as is shown in FIG. 4.

Figure 6:
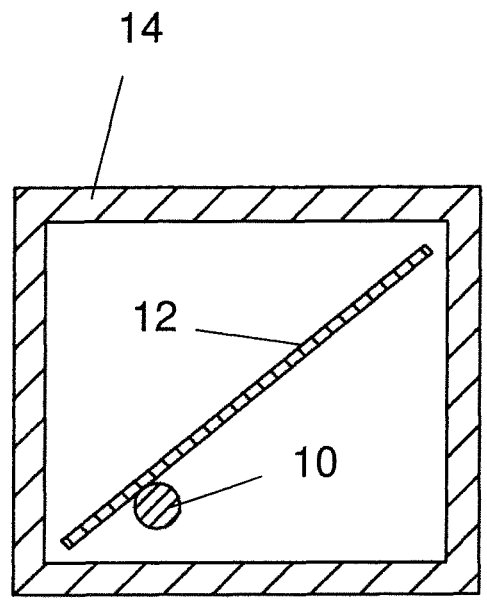
FIG. 6 is a schematic view of the insertion of a valve body into the connection line from the top and from the side.
Figure 7:
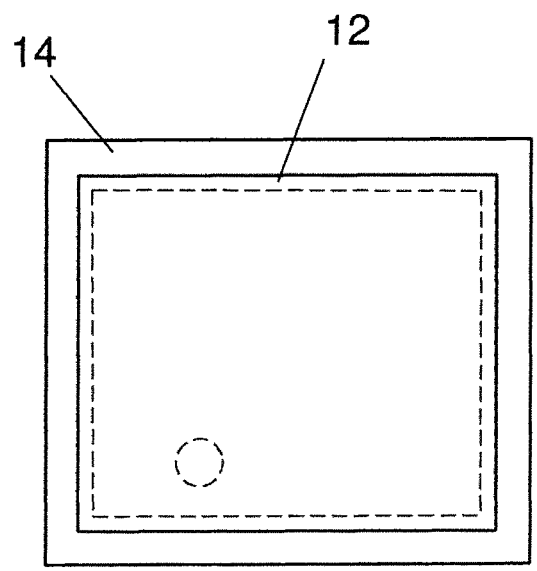
FIG. 7 is the corresponding view after conclusion of the insertion of the valve body.

In an alternative embodiment with an eccentric shaft of valve body 10, the latter can also be inserted into the T-piece without valve disk 12 itself bending during the passage of the connection line and of valve seat 14. In FIGS. 6 and 7, FIG. 6 shows a phase during the pushing in of valve body 10 into the connection line. Valve disk 12 as a whole is bent backward here, so that it can pass through the valve seat. Furthermore, the retracted valve disk 12 is aligned in the diagonal of the rectangular connection line 4 and in the diagonal of the rectangular valve seat 14, so that it can pass through it without bending of valve disk 12 itself. After entry into the interior of the line beyond the valve seat, valve disk 12 again returns into its original position in relation to shaft 10 and can thus be brought into the position shown in FIG. 7, in which it covers the valve seat.

While specific embodiments of the invention have been shown and described in detail to illustrate the application of the principles of the invention, it will be understood that the invention may be embodied otherwise without departing from such principles.

What is claimed is:

1. A self-locking T-piece for connecting an attachment to a breathing gas line, the self-locking T-piece comprising:
    a line section;
    a connection line branching off from the line section;
    a spring;
    a movable valve body with a valve disk body; and
    a valve seat, wherein the valve body is prestressed by the spring into a sealing position with the valve body engaging the valve seat, in which the valve body seals the connection line relative to the line section, and the valve body is moved out of the sealing position when connecting the attachment to the connection line, the valve body being elastically deformable, such that the valve body can be advanced through the connection line and through the valve seat while undergoing elastic deformation and the valve body returns to an original shape during entry of the valve disk body into the line section, the original shape of the valve body having a sufficient extension to be able to cover the valve seat for sealing.

2. A self-locking T-piece in accordance with claim 1, wherein:
    the valve disk body has a smaller external diameter than an internal diameter of the connection line;
    the valve disk body is provided with a collar made of an elastically deformable material, the collar projecting beyond the edge of the valve disk body and having an external diameter that is larger than the internal diameter of valve seat.

3. A self-locking T-piece in accordance with claim 2, wherein the valve disk body and the projecting collar are manufactured in one piece according to a two-component injection molding process, wherein the plastic material in the projecting collar is softer than the plastic material of the valve disk body.

4. A self-locking T-piece in accordance with claim 2, wherein:
    the valve body comprises the valve disk body made of hard plastic material and the collar projecting beyond the hard plastic material, which collar is made of a softer plastic material, wherein the valve disk body and the collar are fitted into each other.

5. A self-locking T-piece in accordance with claim 1, wherein:
    the valve disk body has an external diameter that is larger than an internal diameter of the connection line and is larger than an internal diameter of the valve seat; and
    the valve disk body is formed of material and is dimensioned such that an outer edge of the valve disk body can bend back when the valve body is being advanced through the connection line in order to be able to pass through the connection line and the valve seat.

6. A self-locking T-piece in accordance with claim 1, wherein:
    the valve disk body of the valve body is connected to a shaft of the valve body;
    external dimensions of the valve disk body are larger than dimensions of an opening of the valve seat; and
    the shaft is connected eccentrically to the valve disk body, whereby by bending the shaft, the valve disk body is bent back when the valve body is advanced through the connection line and the valve disk body is bent back when the valve body is advanced through the valve seat.

7. A process for manufacturing a self-locking T-piece for connecting an attachment to a breathing gas line, the process comprising the steps of:
    providing a line section, a connection line branching off from the line section, a spring, a movable valve body with a valve disk body and a valve seat;
    advancing the valve body through the connection line and the valve seat, while the valve body undergoes deformation, until the valve disk body returns to its original shape during entry of the valve disk body into the line section;
    providing that the original shape has a sufficient extension to cover the valve seat for sealing;
    biasing the valve body, by the spring, into a sealing position, in which the valve body seals the connection line with respect to the line section, with the valve disk body in a seated position relative to the valve seat, and the valve body is moved out of the sealing position when connecting the attachment to the connection line.

8. A process in accordance with claim 7, wherein:
    the valve disk body has a smaller external diameter than the internal diameter of the connection line;
    the valve disk body is provided with a collar made of an elastically deformable material, the collar projecting beyond the edge of the valve disk body and having an external diameter that is larger than the internal diameter of valve seat.

9. A process in accordance with claim 8, wherein the valve disk body and the projecting collar are manufactured in one piece according to a two-component injection molding process, wherein the plastic material in the projecting collar is softer than the plastic material of the valve disk body.

10. A process in accordance with claim 8, wherein:
    the valve disk body is formed of hard plastic material and the collar, projecting beyond the hard plastic material, is made of a softer plastic material, wherein the valve disk body and collar are fitted into each other.

11. A process in accordance with claim 7, wherein:
    the valve disk body has an external diameter that is larger than an internal diameter of the connection line and is larger than an internal diameter of the valve seat; and
    the valve disk body is formed of material and is dimensioned such that an outer edge of the valve disk body can bend back when the valve body is being advanced through the connection line in order to be able to pass through the connection line and the valve seat.

12. A process in accordance with claim 7, wherein:
    the valve disk body of the valve body is connected to a shaft of the valve body;
    external dimensions of the valve disk body are larger than dimensions of an opening of the valve seat; and
    the shaft is connected eccentrically to the valve disk body, whereby by bending the shaft, the valve disk body is bent back when the valve body is advanced through the connection line and the valve disk body is bent back when the valve body is advanced through the valve seat.

13. A breathing gas line self-locking T-piece comprising:
a line section;
a connection line branching off from the line section, the connection line having a connection line inner cross sectional dimension;
a spring;
a valve seat connected to the connection line, the valve seat having a valve seat inner cross sectional dimension; and
a valve body positioned for movement within said connection line, the valve body comprising a valve disk, the valve body having an external cross sectional dimension that is greater than the connection line inner cross sectional dimension and greater than the valve seat inner cross sectional dimension, wherein the valve body is biased by the spring into a sealing position with the valve body contacting the valve seat to seal the connection line relative to the line section, and the valve disk is moved out of the sealing position upon the valve body being contacted by an attachment, which is connected to the connection line, the valve body having an elastically deformable portion and having a valve body deformed state in which the valve disk passes through the connection line and the valve seat during assembly and the valve body having a valve body returned state in which the valve body elastically returns to an original shape with the valve disk disposed in the sealing position.

14. A self-locking T-piece in accordance with claim 13, wherein:
the valve disk body has a portion with a smaller external dimension than an internal dimension of the connection line and the elastically deformable portion comprises a projecting collar made of an elastically deformable material, the projecting collar projecting beyond the portion with the smaller external dimension and the projecting collar having an external dimension that is larger than a dimension of an opening of the valve seat.

15. A self-locking T-piece in accordance with claim 14, wherein the valve body is manufactured in one piece according to a two-component injection molding process, wherein the plastic material of the projecting collar is softer than the plastic material of the portion with the smaller dimension.

16. A self-locking T-piece in accordance with claim 14, wherein:
the valve disk body includes a portion made of a hard plastic material and the projecting collar made of a softer plastic material, wherein the projecting collar is fitted onto the portion made of a hard plastic material.

17. A self-locking T-piece in accordance with claim 13, wherein:
the valve disk body has an external dimension that is larger than the an internal dimension of the connection line and is larger than a dimension of an opening of the valve seat; and
the elastically deformable portion comprises an outer edge of the valve disk body that bends back when the valve body is being advanced through the connection line in order to be able to pass through the connection line and to pass through the valve seat.

18. A self-locking T-piece in accordance with claim 13, wherein:
the valve body further comprises a body portion and a shaft portion;
the shaft portion includes the elastically deformable portion;
the shaft portion connects the valve disk body to the body portion;
an external dimension of the valve disk body is larger than an opening dimension of the valve seat; and
the shaft is connected eccentrically to the valve disk body, whereby the shaft is bendable to angle the valve disk body, allowing the valve disk body to advance through the connection line and through the opening of the valve seat.

* * * * *